(12) United States Patent
McGahan

(10) Patent No.: US 7,981,041 B2
(45) Date of Patent: Jul. 19, 2011

(54) SONOGRAPHICALLY GUIDED TRANSVAGINAL OR TRANSRECTAL PELVIC ABSCESS DRAINAGE USING TROCAR METHOD AND BIOPSY GUIDE ATTACHMENT

(75) Inventor: John P. McGahan, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 674 days.

(21) Appl. No.: 12/015,317

(22) Filed: Jan. 16, 2008

(65) Prior Publication Data

US 2008/0171940 A1    Jul. 17, 2008

Related U.S. Application Data

(60) Provisional application No. 60/885,342, filed on Jan. 17, 2007.

(51) Int. Cl.
*A61B 8/00* (2006.01)
*A61B 8/14* (2006.01)
*A61B 17/32* (2006.01)
*A61M 5/00* (2006.01)

(52) U.S. Cl. ........ 600/461; 600/439; 600/459; 600/462; 600/464; 600/471; 604/116; 606/167

(58) Field of Classification Search .............. 600/437, 600/439, 461, 462, 459, 464, 471; 604/116; 606/131
See application file for complete search history.

(56) References Cited

U.S. PATENT DOCUMENTS

| | | | |
|---|---|---|---|
| 4,838,506 A | 6/1989 | Cooper | |
| 5,931,787 A * | 8/1999 | Dietz et al. | 600/461 |
| 5,954,670 A | 9/1999 | Baker | |
| 6,095,981 A | 8/2000 | McGahan | |
| 6,368,280 B1 * | 4/2002 | Cermak et al. | 600/459 |
| 6,443,902 B1 | 9/2002 | Sasady | |
| 6,884,219 B1 | 4/2005 | Pruter | |
| 2002/0123689 A1 | 9/2002 | Furia | |
| 2004/0019299 A1 | 1/2004 | Ritchart et al. | |
| 2005/0090741 A1 | 4/2005 | Kisen et al. | |

OTHER PUBLICATIONS

Casola et al., "Percutaneous Drainage of Tubo-ovarian Abscesses", Radiology, vol. 182, pp. 399-402, (1992).
Butch et al., "Drainage of Pelvic Abscesses through the Greater Sciatic Foramen", Radiology, vol. 158, pp. 487-491 (1986).
Alexander et al., "Transrectal Sonographically Guided Drainage of Deep Pelvic Abscesses", AJR, vol. 162, pp. 1227-1230 (1994).
Kuligowska et al., "Treatment of Pelvic Abscesses: Value of One-Step Sonographically Guided Transrectal Needle Aspiration and Lavage", AJR, vol. 164, pp. 201-206 (1995). McGahan et al., "Pelvic Abscesses: Transvaginal US-guided Drainage with the Trocar Method", Radiology, vol. 200, pp. 579-581 (1996).

(Continued)

*Primary Examiner* — Long V Le
*Assistant Examiner* — Katherine L Fernandez
(74) *Attorney, Agent, or Firm* — John P. O'Banion

(57) ABSTRACT

A needle biopsy guide system is disclosed for attachment to an endoluminal ultrasound probe or like sonographic instrument. The device includes a biopsy-guide attachment that allows for trocar catheter placement for abscess drainage or like procedures, using the transvaginal or transrectal route under sonographic control. The device has a base portion, which is attachable to an ultrasound probe. A removable retainer is provided that slides into the base unit to hold a biopsy needle in place. A physician may locate the target area in the body with the ultrasound probe, insert the biopsy needle into the target area, and then remove the insert (retainer) from the base unit and ultrasound probe, and leave the biopsy needle in place in the body.

23 Claims, 9 Drawing Sheets

OTHER PUBLICATIONS vanSonnenberg et al., "US-guided Transvaginal Drainage of Pelvic Abscesses and Fluid Collections", Radiology, vol. 181, pp. 53-56 (1991).

Lee et al., "Single-Step Transvaginal Aspiration and Drainage for Suspected Pelvic Abscesses Refractory to Antibiotic Therapy", J. Ultrasound Med., vol. 21, pp. 731-738 (2002).

Hovsepian et al., "Transrectal versus Transvaginal Abscess Drainage: Survey of Patient Tolerance and Effect on Activities of Daily Living", Radiology, vol. 212, pp. 159-163 (1999).

Nielsen et al., "Sonographically Guided Transrectal or Transvaginal One-Step Catheter Placement in Deep Pelvic and Perirectal Abscesses", AJR, vol. 183, pp. 1035-1036 (2004).

Varghese et al., "Transvaginal Catheter Drainage of Tuboovarian Abscess Using the Trocar Method: Technique and Literature review", AJR, vol. 177, pp. 139-144 (2001).

Eschelman et al., "Use of a Colapinto Needle in US-guided Transvaginal Drainage of Pelvic Abscesses", Radiology, vol. 186, pp. 893-894 (1993).

* cited by examiner

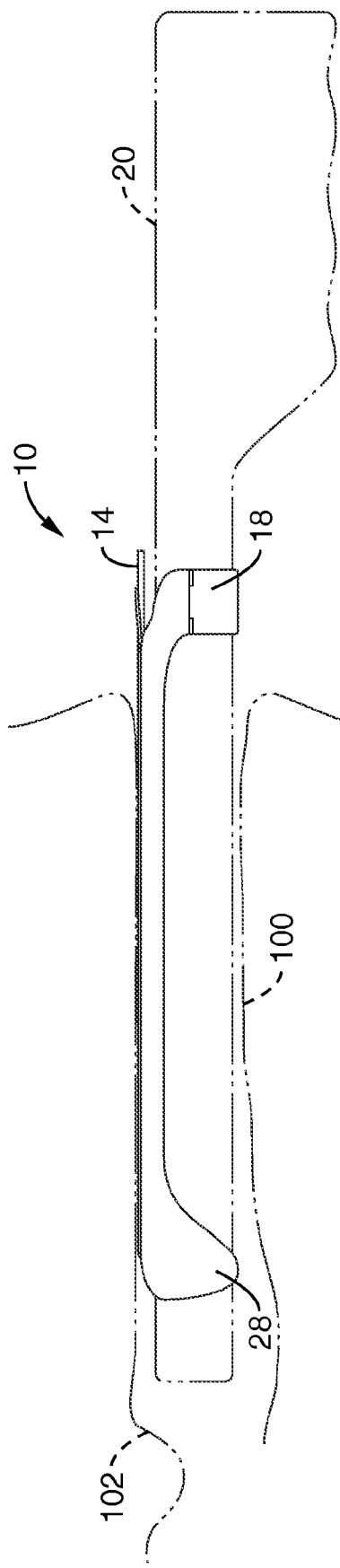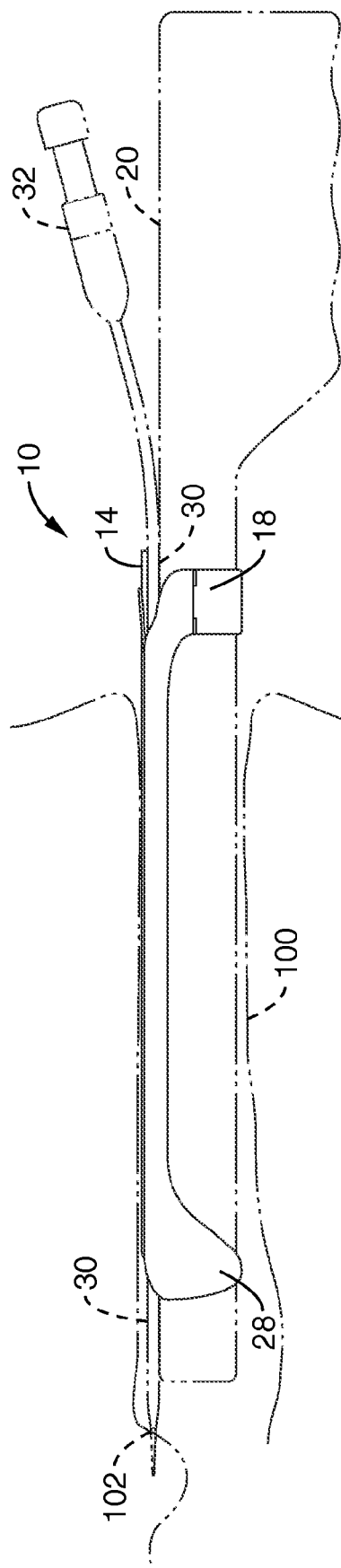

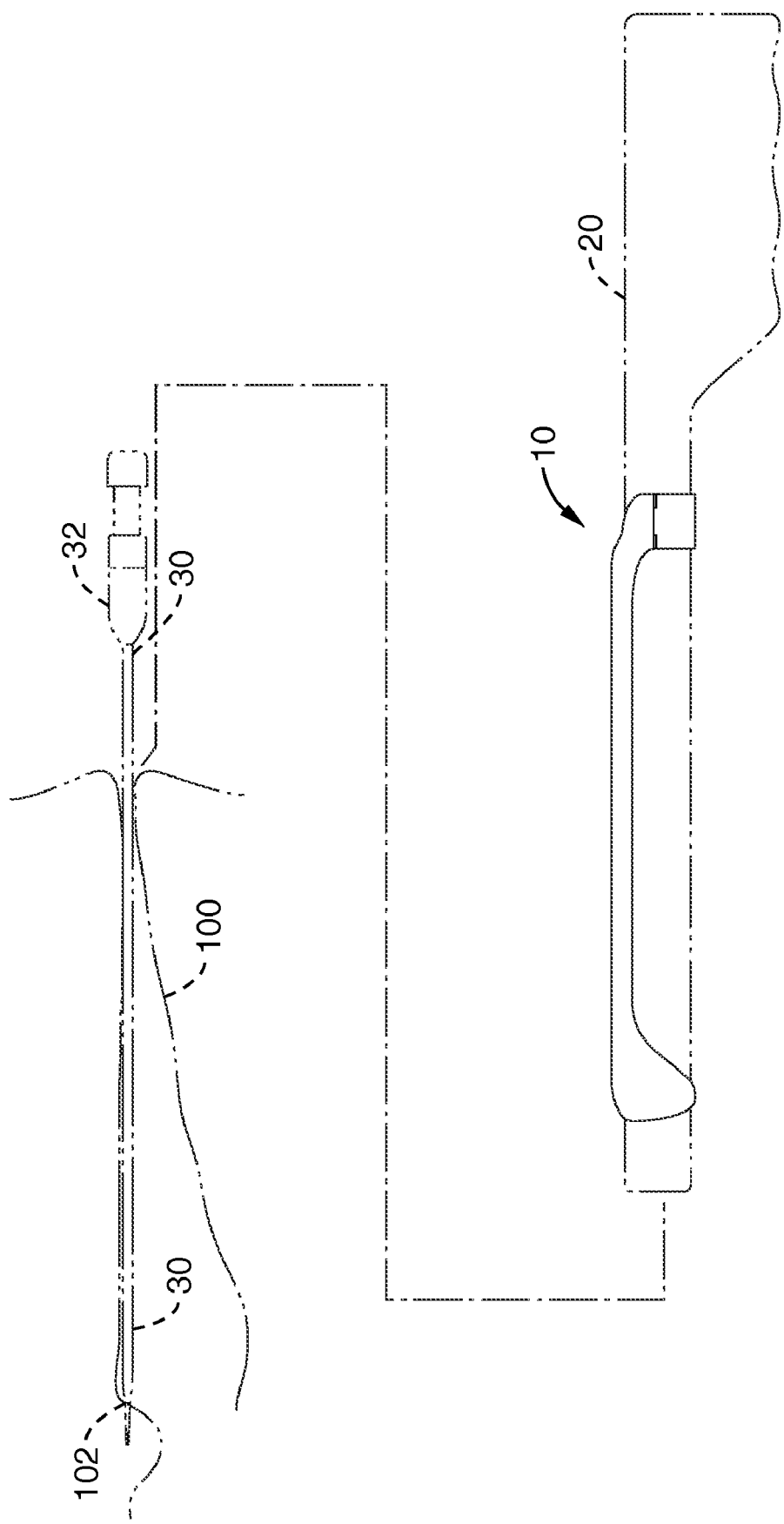

SONOGRAPHICALLY GUIDED TRANSVAGINAL OR TRANSRECTAL PELVIC ABSCESS DRAINAGE USING TROCAR METHOD AND BIOPSY GUIDE ATTACHMENT

CROSS-REFERENCE TO RELATED APPLICATIONS

This application claims priority from U.S. provisional application Ser. No. 60/885,342 filed on Jan. 17, 2007, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to a needle guide, and more particularly to a needle guide for attachment to a medical instrument such as an imaging probe.

2. Description of Related Art

Pelvic inflammatory disease affects nearly 1 million women in the United States annually, and approximately 85,000 of these women eventually have pelvic abscesses. Left untreated, pelvic abscesses are associated with acute morbidity, adhesion formation, impaired fertility, and chronic pelvic pain. Although many pelvic abscesses respond to antibiotic therapy, surgery is often needed when antibiotics fail. However, laparotomy for pelvic abscesses is one of the more technically difficult gynecologic procedures and has associated surgical and anesthetic risks, hospitalization costs, and prolonged recovery times. The definitive surgical treatment of a total hysterectomy and bilateral salpingo-oophorectomy is highly effective. However, the surgical treatment leaves patients infertile and devoid of ovarian hormones, which are major problems in the young premenopausal women who tend to be affected by pelvic abscesses. Total abdominal hysterectomy is the alternative to failed aspiration or drainage of these abscesses.

Pelvis Abscess may also be due to a number of other etiologies. Patients with appendicitis, diverticulitis or Crohn's disease may develop pelvis abscesses. Laparotomy is highly effective in the treatment of these pelvic abscesses. However, laparotomy is associated with both anesthesia and surgical risks, and prolonged recovery time.

Over the past decade, percutaneous image guided drainage of pelvic abscesses has shown to be an effective alternative to surgical techniques [1]. Various approaches have been advocated for drainage of these abscesses, including the transabdominal route, the transgluteal route [2], the transrectal route [3, 4] and the transvaginal route [5, 6]. CT or sonography has been used to guide the transabdominal and the transgluteal abscess drainage. Only sonography is used for guidance of transrectal or transvaginal abscess drainage. However, for sonographically guided transrectal or transvaginal trocar method of needle placement, the use of a punctured channel that is not open to allow the catheter to be free is a technical limitation for all current endorectal and endovaginal transducers.

Therefore, there have been modifications of different transrectal or transvaginal ultrasound probes to allow catheter placement. These have included the use of a catheter, which is placed through a peel-away sheet or catheters that are placed into a groove on the ultrasound probe and are fixed with rubber bands. These allow trocar catheter placement for transrectal or transvaginal drainage [7-10].

Transrectal and/or transvaginal abscess drainage using sonographic technique has been shown to be an effective method in drainage of pelvic abscesses. While CT was previously the method that was utilized for drainage of these abscesses via the transgluteal and/or the transabdominal route, there have been a number of different manuscripts that have described the transrectal or transvaginal sonographic guidance of deep pelvic abscess. [5-10]

When using the transrectal or transvaginal route, aspiration alone has been shown to be as successful when compared with catheter placement. For instance, Lee [7] reported an overall success rate of 86%, using aspiration alone or 86% success rate for catheter placement. Van Sonnenberg [6] has shown an 88% success rate in patients with aspiration alone, compared to 83% with catheter placement. However, patients with aspiration alone may have smaller fluid collections, less loculations or less viscous fluid than those in which catheters are placed. Catheter placement allows repeated flushing of larger abscesses to help breakdown loculi and decrease the viscosity of the abscess contents.

With the Seldinger technique, a needle is placed, and then a guide wire is placed through the needle after removal of the needle stylet. Thus the needle, the needle guide and the ultrasound probe are then removed. The guidewire is kept in place and the rest of the technique may be guided by fluoroscopy or by ultrasound. However, there may be difficulty in catheter placement via the Seldinger technique when using the endovaginal route. This is because of the difficulty with buckling of the guidewire when dilators or catheters are placed through the thick vaginal musculature.

Thus, the invention relates to providing a needle guide for attachment to a sonographic transducer, which allows the probe and needle guide to be detached and removed from the needle or trocar catheter and removed from the patient while the needle or trocar catheter remains in place within the abscess cavity. This will allow for a single step for catheter placement into a pelvic abscess using either the endovaginal or endorectal route.

BRIEF SUMMARY OF THE INVENTION

The present invention includes a needle biopsy guide system, which is configured to be attached to an endoluminal ultrasound probe or like sonographic instrument or imaging probe. The system has a biopsy-guide attachment that will allow for trocar catheter placement for abscess drainage, using the transvaginal or transrectal route under sonographic control.

The system has a base portion, which is attachable to an ultrasound probe. A removable insert or retainer is provided that slides into the base unit to hold a biopsy needle in place. In an exemplary preferred method, a physician may locate the target area in the body with the ultrasound probe, insert the biopsy needle into the target area, and then remove the insert (retainer) from the base unit and ultrasound probe, and leave the biopsy needle in place in the body.

An aspect of the invention is a needle guide for use with an imaging probe, such as an ultrasound transducer or the like. The needle guide includes an elongate guide body configured to mount to the imaging probe. The guide body has a groove running generally longitudinally along the length of the guide body. The groove is configured to guide translation of a needle along the guide body to a treatment location in a body lumen of a patient. The needle guide further includes a slot running adjacent to the groove, wherein the slot is configured to house a retainer. The retainer is configured to slideably mate with the slot such that the retainer may be removed from the guide body to expose the groove, thereby allowing the needle to be separated from the guide body and imaging probe while the needle remains located at the treatment location.

In an exemplary preferred embodiment, the guide body comprises an inner surface configured to conform to the shape of the imaging probe. The guide body may also have a fastening mechanism to secure the needle guide to the imaging probe.

In another embodiment, the guide body includes an outer surface opposite the inner surface, such that the groove opens longitudinally out into the outer surface via the slot. When the retainer is not installed in the needle guide, the needle may be laterally repositioned from the groove to a location outside the needle guide.

In another embodiment, the guide body has a proximal end and a distal end, wherein the slot is configured such that the retainer may be installed in the needle guide by positioning the retainer in a slot opening at the proximal end of the guide body, and sliding the retainer in the slot longitudinally along the guide body toward the distal end of the guide body. The slot may preferably terminate at a stop at the distal end of the guide body such that the retainer is restrained from forward motion past the stop and the distal end.

In one mode, the groove emanates at a proximal opening of the proximal end and continues through the guide body to terminate at a distal opening at the distal end. The guide body has a depression adjacent to the proximal opening of the groove to allow manipulation of the needle.

Another aspect of the present invention is a method for inserting a biopsy needle at a treatment location in a patient's body. The method includes the steps of attaching a needle guide to an imaging probe, positioning the needle guide and imaging probe at the treatment site in the patient's body, guiding the biopsy needle longitudinally along a groove in the needle guide to the treatment location, slideably removing a retainer from a stowed position in the needle guide to expose the groove, and separating the biopsy needle from the needle guide by laterally pulling it out of the exposed groove. The needle guide and biopsy probe may then be removed from the treatment location while the biopsy needle remains at the location. The biopsy needle, for example, may be guided to the treatment location in an endorectal procedure or an endovaginal procedure.

In one embodiment, the retainer, in the stowed position, is held in a groove adjacent to the slot, such that the biopsy needle is retained in the needle guide when the retainer is in the stowed position. In this configuration, the needle is free to laterally advance away from the needle guide when the retainer is in a retracted position.

Another aspect of the present invention is an apparatus for guiding a needle along an imaging probe to a treatment location in a patient's body. The apparatus has an elongate guide body configured to mount to the exterior surface of an imaging probe. The guide body includes a longitudinal groove spanning an exterior surface of the guide body, wherein the groove is configured to guide translation of a surgical needle longitudinally along the guide body to a treatment location in a body lumen of a patient. The apparatus may further include a slot spanning adjacent and exterior to the groove along the exterior surface of the guide body to house a retainer. The retainer may be configured to slideably mate with the slot such that the retainer may be removed from the guide body to expose the groove, thereby allowing the surgical needle to be separated from the guide body and imaging probe while the needle remains located at the treatment location.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 9A is a side view of the needle guide and transducer of FIG. 1 being inserted in a body lumen.

FIG. 9B is a side view of the needle guide and transducer of FIG. 1 being used to guide a biopsy needle to a treatment location in the body lumen.

FIG. 9D illustrates removal of the needle guide and transducer from the body lumen while the needle remains at the treatment location in the body lumen.

DETAILED DESCRIPTION OF THE INVENTION

Referring more specifically to the drawings, for illustrative purposes the present invention is embodied in the apparatus generally shown in FIG. 1 through FIG. 9D. It will be appreciated that the apparatus may vary as to configuration and as to details of the parts, and that the method may vary as to the specific steps and sequence, without departing from the basic concepts as disclosed herein.

Figure 1:
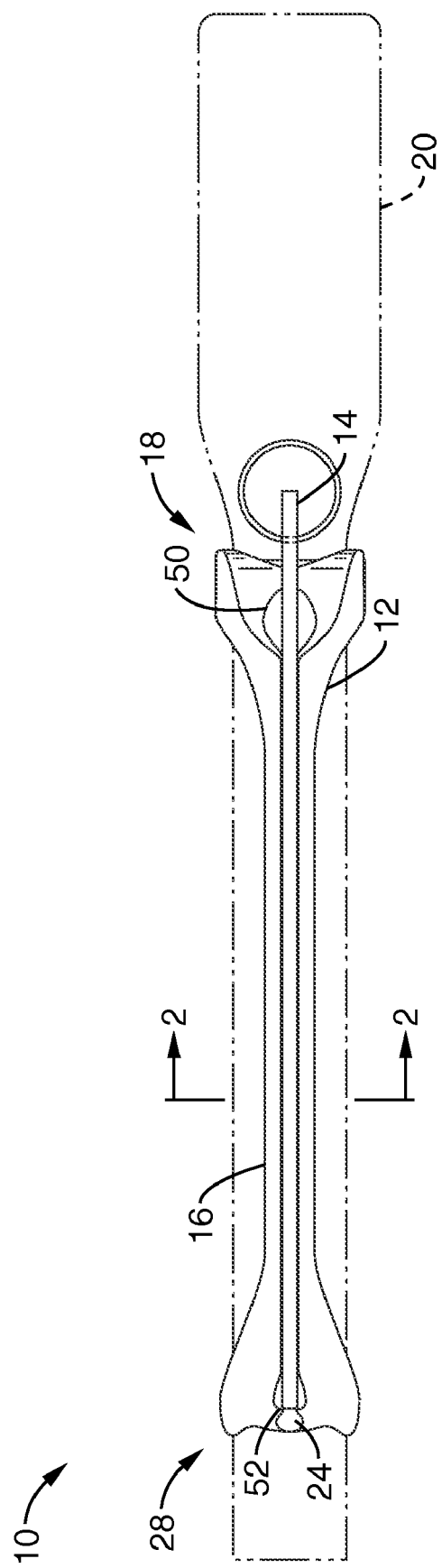
FIG. 1 is a top view of the needle guide of the present invention installed on an ultrasound transducer.

FIG. 1 illustrates a top view of a needle guide 10 configured to attach to a diagnostic instrument 20, such as an ultrasound probe (transducer) or the like. Needle guide 10 primarily includes a guide body 12 and a retainer 14 that is configured to slide longitudinally, i.e. along the length of the guide body 12, into a slot 16 that runs along the top of guide body 12.

Figure 2:
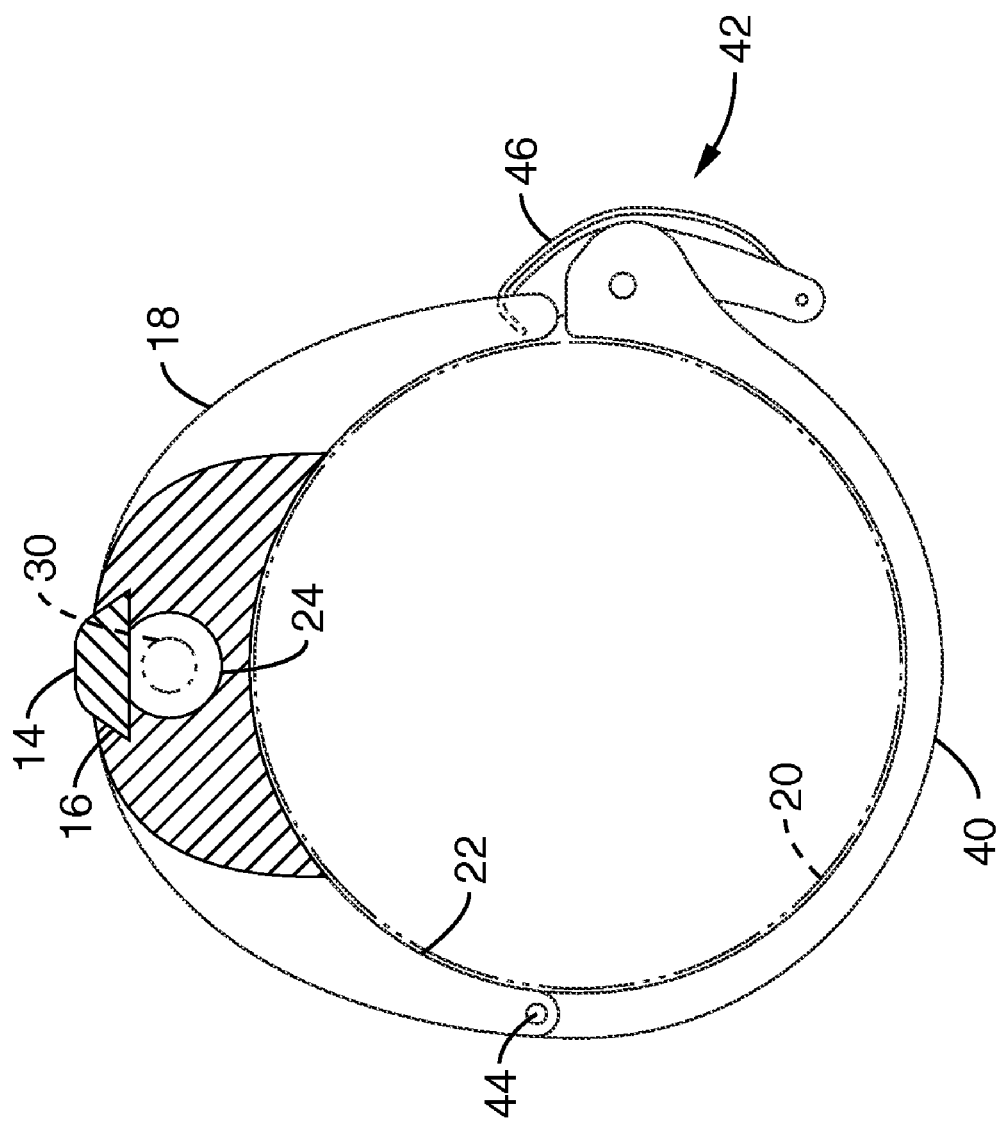
FIG. 2 is a cross sectional view of the needle guide and transducer of FIG. 1, with a biopsy needle installed in the guide.
Figure 4:
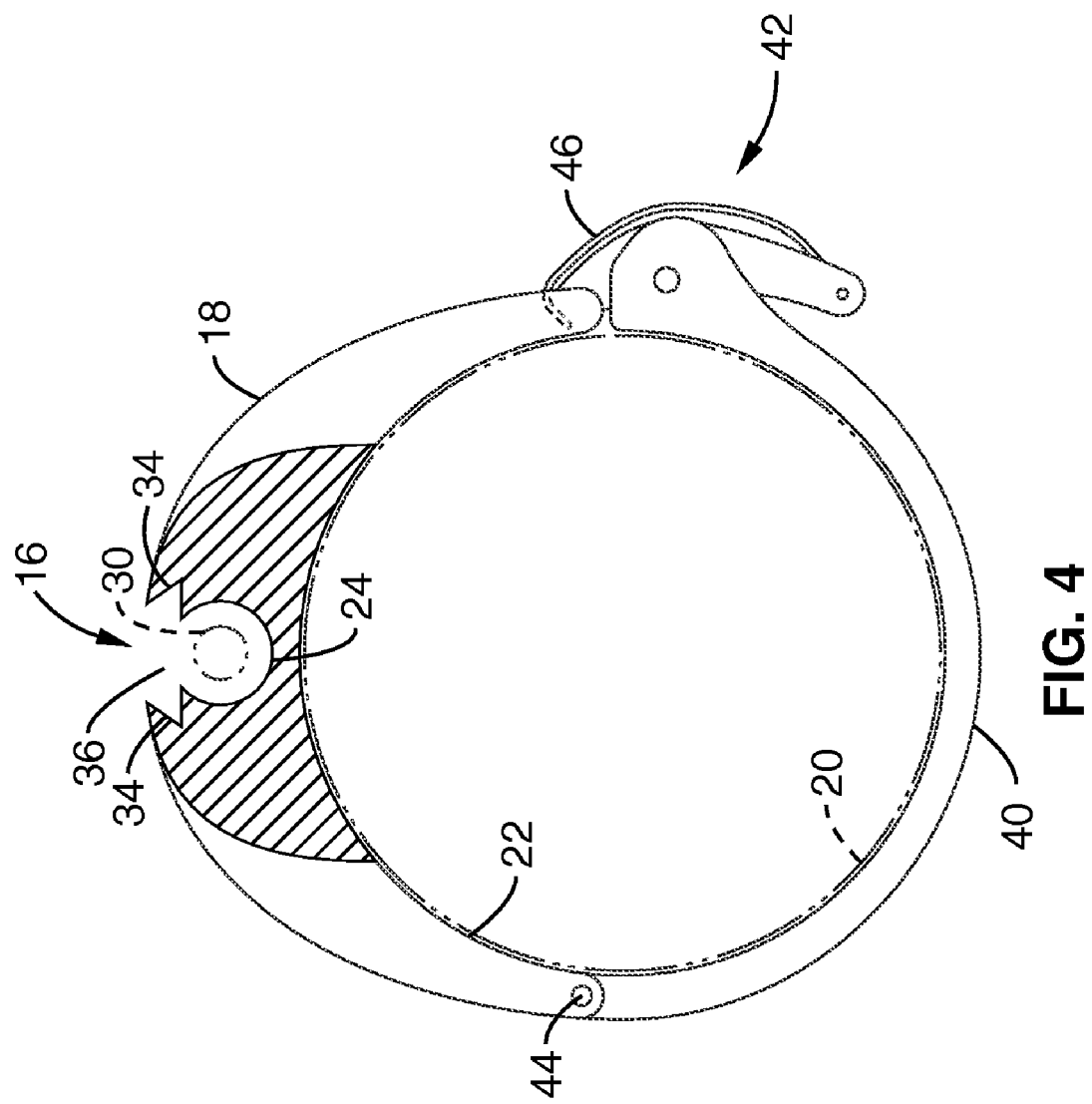
FIG. 4 is a cross sectional view of the needle guide and transducer of FIG. 1, with the retainer removed.

FIG. 2 illustrates further detail of the guide body 12 in cross-sectional view with the retainer 14 inserted. As shown in FIGS. 2 and 4, the slot 16 is preferably configured to have sidewalls 34 that that are sloped to form an acute angle such that the retainer 14 is retained from moving upward when installed in the slot. Slot 16 is preferably sized to house retainer 14 without lateral play so as to maintain placement accuracy without frictional engagement that would impede removal of the retainer from the slot or placement of the retainer into the slot.

The body 12 also has groove 24 that runs below and generally longitudinal with slot 16. As shown, groove 24 is generally circular in shape, however, groove 24 may comprise a variety of geometries to allow needle 30 to be freely inserted and directed. The term "needle" as used herein encompasses biopsy needles, trocar catheters or like hollow instruments for introducing material into or removing material from the body. In some embodiments, the present invention also may be used to guide other elongate medical instruments, which may or may not be hollow. Groove 24 of needle guide 10 is configured to position needle 30 in a longitudinal orientation in relation to instrument 20 when the retainer 14 is inserted in the guide body 12.

Figure 3:
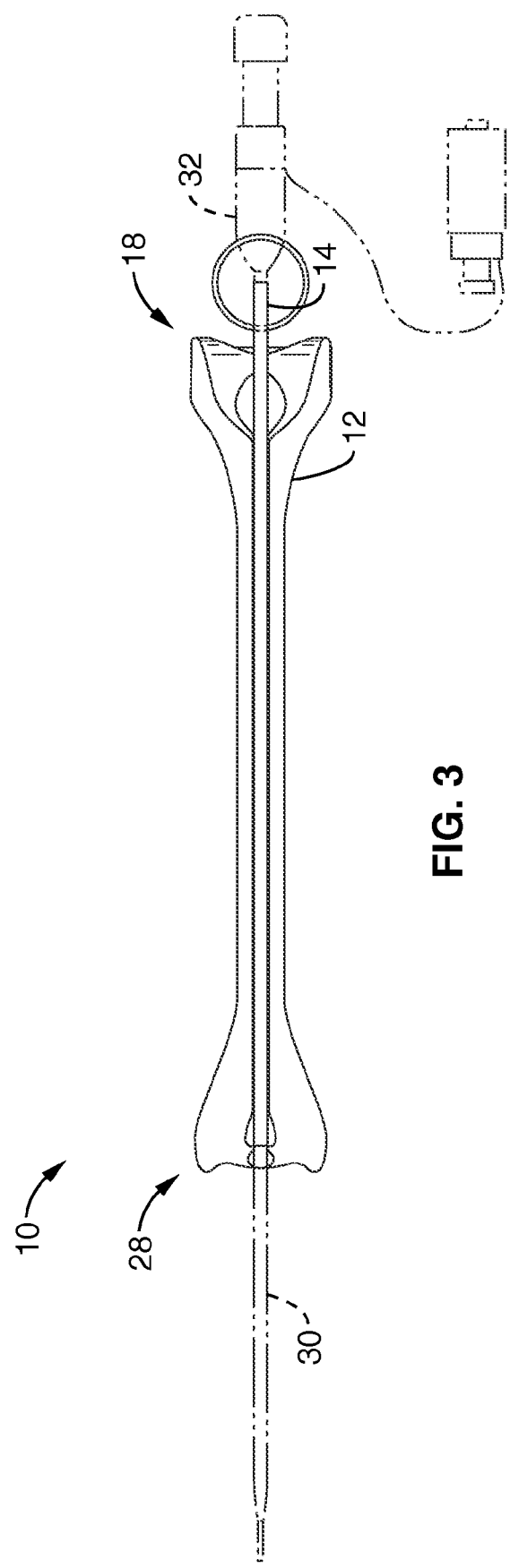
FIG. 3 is a top view of the needle guide and transducer of FIG. 1, with a biopsy needle installed in the guide.

FIG. 3 shows a top view of the needle guide 10 carrying a conventional needle 30 having a hub 32. Those skilled in the art will appreciate that hub 32 prevents conventional needle carrier/transducer assemblies from being removed from a body cavity without engaging hub 32 and removing needle 30 at the same time.

As shown in FIG. 3 (and in cross section in FIG. 2), the presence of the retainer 14 in the slot 16 over groove 24 provides an enclosed, longitudinal path running generally axially down the length of the guide body 12 (and thus the instrument 20). Thus, for example, by inserting a needle, or trocar catheter 30 into the proximal end 18 of the groove 24, the forward motion of the needle 30 is confined to be longitudinal along the groove, without obstruction, and precisely directed to the distal end 28 of the guide 10 and probe 20.

Because the hub 32 has a generally larger profile than the groove 24, it precludes the guide 10 (and instrument 20) from being backed away or separated from the needle 30 while the needle remains at the treatment site. To facilitate this, the retainer 14 is removed from the guide body 12 to expose the open end of groove 24.

Figure 5:
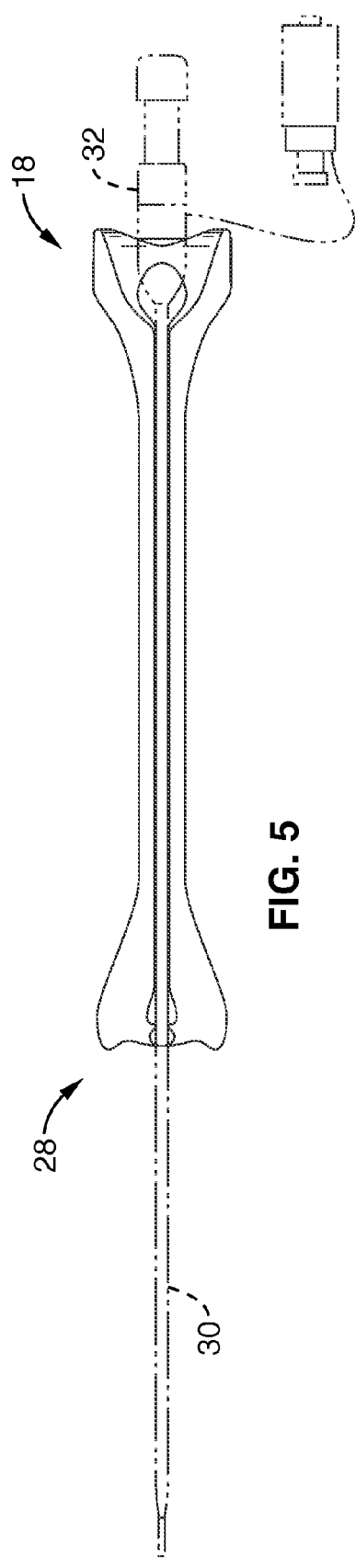
FIG. 5 is a top view of the needle guide and transducer of FIG. 1, with the retainer removed.

FIGS. 4 and 5 provide further detail of the guide body 12 in cross-sectional view with the retainer 14 removed. As shown in FIG. 4, the upper end of groove 24 opens into slot 16, such that needle 30 may be separated from the guide body 12 via a lateral, or non-longitudinal, motion of the guide body 12 with respect to the needle 30. Once the needle 30 is outside the confines of the slot 24, the guide 10 and instrument 20 may be longitudinally extracted from the treatment site while the needle 30 remains in place.

Figure 6:
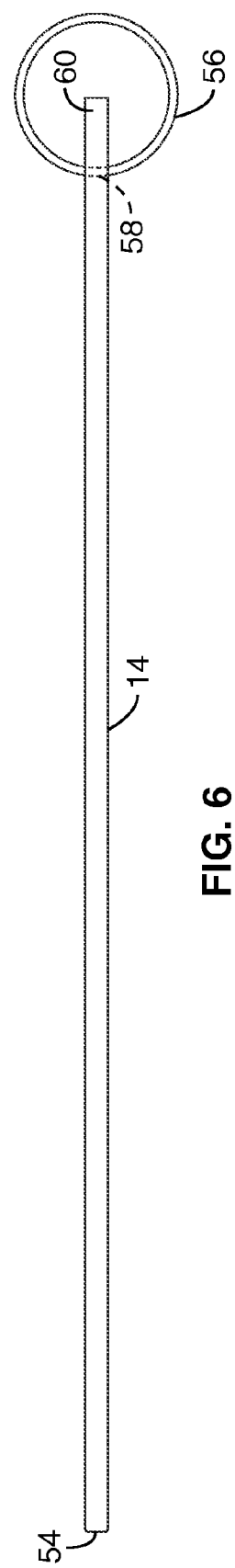
FIG. 6 is a top view of the retainer of the present invention.

FIG. 6 illustrates a top view of the retainer 14. The retainer 14 is a generally elongate member that is configured to extend the length of slot 16 so that a portion of the proximal end 60 of the retainer preferably extends past the proximal end of the guide body 12. The distal tip 54 of the retainer is preferably tapered to allow it to be readily placed into slot 16 with minimal guidance. The remainder of the retainer 14, out to the proximal end 60, then takes a profile that generally matches the internal walls of the slot 16, such that the retainer is restrained from lateral motion once inside the slot 16, but freely moves longitudinally inside slot 16. As shown in the cross section of FIG. 2, the sides of the retainer 14 may generally form a trapezoidal shape, in part to match the walls of the slot 16. However, it is appreciated that the retainer may be configured to conform to a number of different shapes, e.g. circular, semi-circular, elliptical, etc., with corresponding matching internal walls for slot 16.

The retainer 14 also may comprise a pull ring 56 that is retained inside a bore 58 of the retainer 14. The pull ring 56 facilitates digital maneuvering of the retainer 14 in and out of the slot 16.

Figure 7:
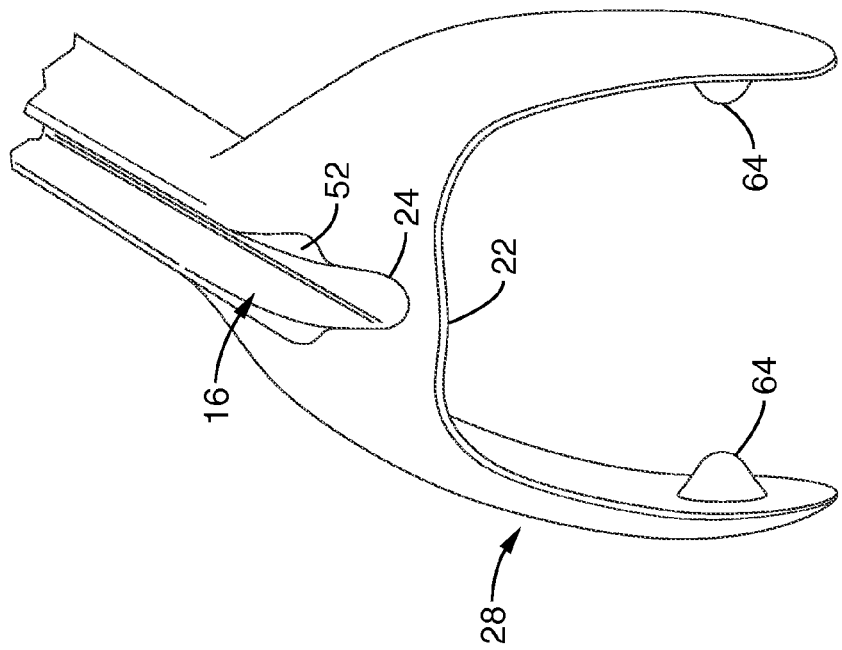
FIG. 7 is a perspective view of the distal end of the needle guide without the retainer.

Referring now to FIG. 7, the slot 16 terminates at stop 52 just short of the distal tip 28 of the guide body 12. Stop 52 prevents forward motion of the retainer 14 with respect to the guide body 12 once the retainer has been installed along the length of the slot 16. Thus, when the retainer 14 has been fully installed in guide body 12, it is only free to move in one direction, i.e. it can only move longitudinally outward from the proximal end 18 of the guide.

Figure 8:
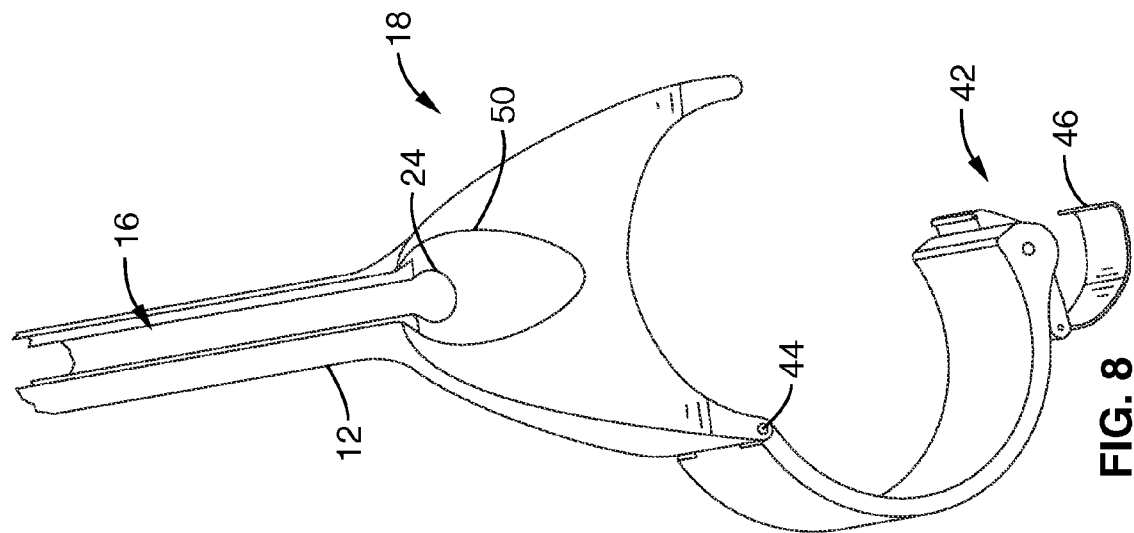
FIG. 8 is a perspective view of the proximal end of the needle guide without the retainer.

Referring now to FIG. 8, the proximal end 18 of the guide body 12 has a recess 50 emanating from the exit point of groove 24 and slot 16. Recess 50 allows the needle 30 and hub 32 to be deflected downward so that the retainer may clear the hub 32 and be removed from the guide body 12.

Referring back to FIG. 2, guide 10 preferably may be coupled to instrument 20 by a coupling means, such as a ring shaped fastener 40, which is positioned at the proximal end 18 of the guide body 12. It will be appreciated that any number of rings, including a second ring at the distal end 28 (not shown), could be used as well without departing from the scope of the invention. Instrument 20 fits within rings 40, and the longitudinal position of the apparatus in relation to instrument 20 is held fixed by locking means 42, that has a cam-type latch 46 which may be used to secure the guide 10 to the instrument 20. To release the guide 10 from the instrument 20, the latch 46 may be pulled back to allow the ring to rotate open along hinge 44.

The guide body 12 with ring 40 generally comprises an internal surface 22 that conforms to the shape of the instrument 20, and may be configured to accommodate a variety of instruments and geometries. Referring to FIG. 7, the distal tip may have a pair of protrusions 64 located on the internal surface. The protrusions 64 may be used to lock into a groove or other feature of the instrument 20.

Additionally, the locking means 42 could alternatively comprise a set screw or any other type of fastener, although it is preferred that the fastener be of a type that allows the ring to be disconnected or disengaged from the transducer. It will also be appreciated that other detachable coupling means, such as slotted joints (e.g., dovetail or dado-like joints), adjustable circumference bands or the like, could be employed to fasten needle guide 10 to instrument 20 instead of using ring 40.

FIGS. 9A-9B illustrate a method of guiding a needle into a body lumen, e.g. for transrectal or transvaginal pelvic abscess drainage. As shown in FIG. 9A, the needle guide 10 of the present invention is installed on the ultrasound transducer 20 and inserted (e.g. endovaginally or endorectally) into the body cavity 100. The ultrasound probe 20 (or other similar device known in the art) is used to guide placement of the distal tip 28 of the guide to the appropriate region, i.e. treatment area 102 where the abscess is located. The needle guide 10 is preferably long enough so that the proximal end 18 of the guide body 12, bearing the groove 24, and retainer 14, is external to the patient for access by the physician.

Referring now to FIG. 9B, after localizing the abscess cavity and ensuring there are no large vessels in its path for example by using color flow, a trocar catheter 30 (or similar device) is then placed through groove 24 of the needle guide 10 at the proximal end 18, guiding the biopsy needle to a treatment location 102 in the body lumen 100. The catheter or needle 30 exits the guide 10 at the distal end 28 and into the treatment location. Once the trocar catheter 30 has been placed, the inner stylet (not shown) is removed and the fluid is aspirated. If purulent fluid is aspirated, then the catheter 30 may be pushed from the stiffening canula into the fluid collection. The Cope loop of the catheter is then tightened.

Figure 9C:
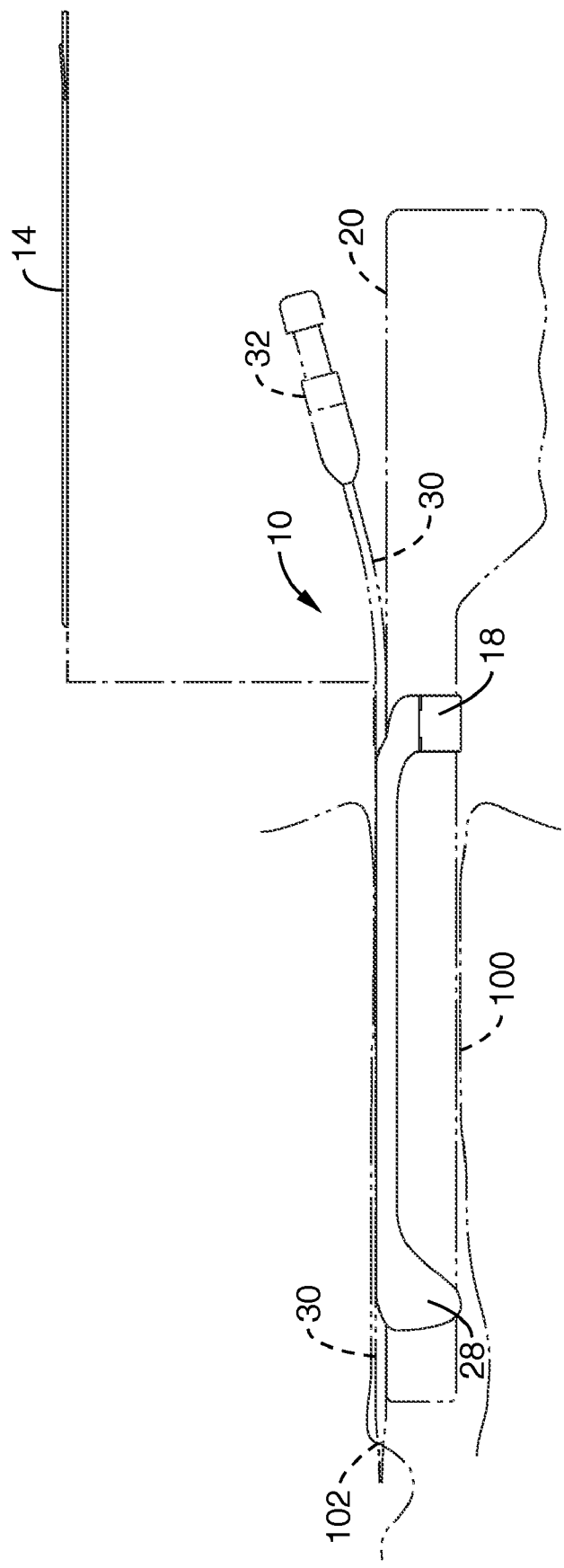
FIG. 9C illustrates removal of the retainer from the needle guide and transducer and separation of the biopsy needle from the needle guide and transducer while the needle remains at the treatment location in the body lumen.

As shown in FIG. 9C, the retainer 14 is removed from the needle guide 10 by sliding it out from the slot 16. Pulling on loop 56 may facilitate this. With the retainer 14 removed, the upper end of groove 24 opens to allow separation of the catheter 30 from the needle guide 10 and transducer 20, allowing the catheter 30 to remain at the treatment location 102 in the body lumen.

Referring now to FIG. 9D, the needle guide 10 and transducer 20 may then be removed from the body lumen 100 while the catheter 30 remains at the treatment location 102 in the body lumen.

Test Setup and Results

Nine patients, in whom a new biopsy guide was used for endorectal or endovaginal drain, are presented. The pelvic abscesses in all patients were non-responsive to antibiotics. Most patients received double antibiotic treatment or triple antibiotic therapy (see Table I). The indication for abscess drainage, includes patients who were septic after suspected abscess after appendectomy (n=3) post surgical, (n=2) diverticulitis, (n=2) and tubal ovarian abscess (n=2). Catheters were placed via the trocar method, using the transrectal route in 6 cases and in the endovaginal route in 3 cases. All patients had received deep conscious sedation with Midazolam hydrochloride (Versed; Hoffman-LaRoche, Inc., Nutley, N.J.) with fentanyl citrate (Abbott Laboratories, Abbott Park, Ill.) using an endovaginal probe CEV-8C4 EC7-Acuson (Acuson, Inc., Mountain View, Calif.).

A biopsy guide 10 as shown in FIGS. 1-9D was used, and included a central groove 24 for catheter placement and a removable retainer 14 that could be detached from guide 10 after catheter placement. The biopsy guide 10 was large enough to allow trocar placement of a 6.7 French-McGahan catheter (Cook Surgical, Bloomington, Ind.). Once the ultrasound probe was placed, either into the vagina or to the rectum, the trocar technique was used to place the catheter in the fluid collection.

When placing the catheter via the endovaginal or the endorectal technique, color flow Doppler ultrasound was utilized to avoid vessels in the intervening path. The inner stylet of the trocar catheter was removed after entering the fluid collection, and fluid aspiration was performed. In all cases, the catheter was then placed after aspiration of turbid or purulent fluid and the fluid was completely drained. The catheter was then placed to a Jackson-Pratt bulb syringe. The catheter was irrigated every shift with normal saline.

Patients continued with antibiotic therapy, which was followed and adjusted based upon the results of the culture. The catheter was removed after patients became afebrile for 24 hours, had a normal white count in drainage less than 10 mls per day, and showed a decrease in abscess cavity on CT. The patients were then followed, clinically, after catheter removal.

Eight of 9 patients had successful aspiration and drainage of fluid collections under ultrasound guidance using the method of the present invention. In one patient, the catheter was successfully placed into a suspected pelvic hematoma that did not decrease significantly in size with drainage. Turbid or purulent fluid was obtained in 8 of 9 patients. The cultures of these abscesses are shown in Table 1.

All patients improved clinically and were later discharged from the hospital. One patient (#8) with an infected hematoma did not respond to catheter drainage and required surgery. Catheter removal occurred from 2 to 11 days not counting the one unsuccessful drainage of a pelvic hematoma. No complications were encountered in any of these patients.

The following references are incorporated by reference in their entirety:
1. Casola G, vansomenberg E, D'Agostino H B, Harker C P, Varney R R, Smith D. Percutaneous drainage of tuboovarian abscesses. Radiology. 1992 February; 182(2):399-402
2. Butch R J, Mueller P R, Fermcci J T Jr, Wittenberg J, Simeone J F, White E M, Brown A S. Drainage of pelvic abscesses through the greater sciatic foramen. Radiology. 1986 February; 158(2):487-91.
3. Alexander P L P L, Eschelman D J, Nazarian L N, Bonn J. Transrectal sonographically guided drainage of deep pelvic abscesses. AJR Am J Roentgenol. 1994 May; 162(5): 1227-30; discussion 123 1-2.
4. Kuligowska E, Keller E, Fermcci J T. Treatment of pelvic abscesses: value of one-step sonographically guided transrectal needle aspiration and lavage. AJR Am J. Roentgenol. 1995 January; 164(1):201-6
5. McGahan J P, Brown B, Jones C D, Stein M. Pelvic abscesses: transvaginal US-guided drainage with the trocar method. Radiology. 1996 August; 200(2):579-81.
6. Vansomenberg E, D'Agostino H B, Casola G, Goodacre B W, Sanchez R B, Taylor B. US-guided transvaginal drainage of pelvic abscesses and fluid collections. Radiology. 1991 October; 181(1):53-6.
7. Lee B C, McGahan J F, Bijan B. Single-step transvaginal aspiration and drainage for suspected pelvic abscesses refractory to antibiotic therapy. J Ultrasound Med. 2002 July; 21(7):731-8.
8. Hovsepian D M, Steele J R, Skinner C S, Maiden E S. Transrectal versus transvaginal abscess drainage: survey of patient tolerance and effect on activities of daily living. Radiology. 1999 July; 212(1): 159-63.
9. Nielsen M B, Torp-Pedersen S. Sonographically guided transrectal or transvaginal one-step catheter placement in deep pelvic and perirectal abscesses. AJR Am J Roentgenol. 2004 October; 183(4): 1035-6.
10. Varghese J C, O'Neill M J, Gervais D A, Boland G W, Mueller P R. Transvaginal catheter drainage of tuboovarian abscess using the trocar method: technique and literature review. AJR Am J Roentgenol. 2001 July; 1 77(1): 139-44. Review.
11. Eschelman D J, Sullivan K L. Use of a Colapinto needle in US-guided transvaginal drainage of pelvic abscesses. Radiology. 1993 March, 186(3):893-4.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

wherein the slot is located substantially parallel and external to the groove such that the retainer, when retained in the slot, blocks the longitudinal opening along at least a substantial portion of the length of the longitudinal opening;

wherein the retainer slideably mates with the slot such that the retainer may be selectively removed from the guide body to expose the groove, thereby allowing the needle to be separated from the guide body and imaging probe while the needle remains located at the treatment location.

2. The needle guide as recited in claim 1, wherein the guide body comprises an inner surface that conforms to the shape of the imaging probe.

3. The needle guide as recited in claim 2, wherein the guide body comprises a fastening mechanism to secure the needle guide to the imaging probe.

TABLE 1

| Pat # | Hx | Size | Drains | Cx (transrectal/vag only) | Abx Pre-drain | Surg Post | Pt Outcome | Days |
|---|---|---|---|---|---|---|---|---|
| 1 | s/p appy perf | 3.5 × 4 | 1. transrectal deep pelvic 6.7F<br>2. LLQ 6F McGahon<br>3. Low central abd 8F APD | *Enterobacter cloacae*<br>*Keibsiella pneumonia*<br>*Psuedomonas auruginosa* | Ampicillin<br>Flagyl<br>Gentamycin | No | CT significant improvement of pelvic abscess | 8 |
| 2 | s/p appy perf | 3 × 4 | Transrectal 6.7F McGahon | *E. coli*<br>*Staphlococcus*, coag(−) | Cefotaxime<br>Flagyl | No | CT drain in place, abscess significant improvement | 6 |
| 3 | s/p appy perf | 5 × 6 | 1. Transrectal 6.7F McGahon<br>2. RLQ 10F Dawson-Meuller | *Strep viridans* | Unknown | No | Drain removed prior to d/c | 3 |
| 4 | R TOA | 4 × 5 | Transvag 6.7F | *E. coli*<br>*Keibsiella* species | Clyndamycin<br>Gentamycin | No | Cath removed by clin. Request for pt d/c. US showed improvement, but fluid still 9.6 cm | 2 |
| 5 | s/p diverticulitis | 5 × 19 | Transvag 6.7F | *Staph*, coag negative | Unknown | No | CT resolved abscess pt d/c | 2 |
| 6 | s/p MVA multiple abscesses, feeding tube misplacement | 2 × 4.5 | 1. Transrectal 6.7F<br>2. Midline 8F pigtail<br>3. L subdiaphragmatic 8.2F pigtail | *Psuedomonas auruginosa* | Metronidazole<br>Cipro<br>Fluconazole<br>Tobramycin | No | CT improvement, CT resolved. Drain still in place | 11 |
| 7 | s/p pelvic surg | 2.5 × 6 | 1. Transrectal 7F loop (lamba)<br>2. LLQ CT 12F loop (lamba) | Gram(−) rod, lactulose+ | Ampicillin<br>Gentamycin<br>Flagyl | No | Drains removed | 9 |
| 8 | s/p diverticulitis perf | 4 × 6 | Transrectal 6.7F McGahon into R pararectal infected hematoma | Nonsporeforming gram+ rod<br>*Enterococcus* species<br>*Bacteroides fragiles*<br>*Clostridium*<br>*Psuedomonas auruginosa*<br>*Lactobacillius*<br>*Provotella/bacteroides* | Unclear, started w/ Cefotaxime Flagyl Long Hospital course-on many Abx | Yes* | Long Hospital course, several surgeries, multiple abscess drainages* because hematoma not resolved | |
| 9 | tubovarian abscess | 5 × 9 | Transvag 6.7F McGahon into peri ovarian abcess | *Bacteroides uniformis*<br>Mixed flora | Unknown | No | US demonstrated resolution | 8 |

What is claimed is:

1. A needle guide for use with an imaging probe, comprising:
   an elongate guide body configured to mount to the imaging probe;
   the guide body having a groove running generally longitudinally along a substantial portion of the length of the guide body;
   the groove having a longitudinal opening extending longitudinally along the groove;
   wherein the groove is configured to guide translation of a needle along the guide body to a treatment location in a body lumen of a patient;
   an elongate retainer; and
   a slot running adjacent to the groove, the slot configured to receive the retainer;

4. The needle guide as recited in claim 3, wherein the fastening mechanism clamps to an external surface of the imaging probe.

5. The needle guide as recited in claim 2:
   wherein the guide body comprises an outer surface opposite the inner surface; and
   wherein the groove opens longitudinally out into the outer surface via the opening adjacent said slot such that, when the retainer is not installed in the needle guide, the needle may be laterally repositioned from the groove to a location outside the needle guide.

6. The needle guide as recited in claim 2:
   wherein the guide body has a proximal end and a distal end; and
   wherein the retainer is configured to be installed in the needle guide by positioning the retainer in an axial slot opening at the proximal end of the guide body, and sliding the retainer in the slot longitudinally along the guide body toward the distal end of the guide body.

7. The needle guide as recited in claim 6, wherein the slot terminates at a stop at the distal end of the guide body such that the retainer is restrained from forward motion past the stop and the distal end.

8. The needle guide as recited in claim 6:
wherein the groove emanates at a proximal opening of the proximal end and continues through the guide body to terminate at a distal opening at the distal end; and
wherein the guide body comprises a depression adjacent to the proximal opening of the groove to allow manipulation of the needle.

9. A method for inserting a biopsy needle at a treatment location in a patient's body, comprising:
attaching a needle guide to an imaging probe;
positioning the needle guide and imaging probe at the treatment location in the patient's body;
guiding the biopsy needle longitudinally along a groove in the needle guide to the treatment location;
the groove having a longitudinal opening extending longitudinally along the length of the groove;
slideably removing a retainer along a slot in the needle guide from a stowed position in the needle guide to expose the longitudinal opening in the groove;
wherein the slot is located parallel and external to the groove such that the retainer, in the stowed position, blocks the longitudinal opening along at least a substantial portion of the length of the longitudinal opening; and
separating the biopsy needle from the needle guide by laterally pulling the biopsy needle out of the exposed groove through the longitudinal opening.

10. The method as recited in claim 9, further comprising:
removing the needle guide and biopsy probe from the treatment location while the biopsy needle remains at the location.

11. The method as recited in claim 9, wherein attaching a needle guide to an imaging probe comprises attaching the needle guide to an ultrasound transducer.

12. The method as recited in claim 9, wherein attaching a needle guide to an imaging probe comprises securing the needle guide to the imaging probe with a fastening mechanism.

13. The method as recited in claim 9:
wherein the retainer, in the stowed position, is held in a dovetail slot adjacent to the groove, such that the biopsy needle is retained in the needle guide when the retainer is in the stowed position, and
wherein the needle is free to laterally advance away from the needle guide when the retainer is in a retracted position.

14. The method as recited in claim 9, wherein the biopsy needle is guided to the treatment location in an endorectal procedure.

15. The method as recited in claim 9, wherein the biopsy needle is guided to the treatment location in an endovaginal procedure.

16. An apparatus for guiding a needle along an imaging probe to a treatment location in a patient's body, comprising:
an elongate guide body configured to mount to the exterior surface of an imaging probe;
the guide body having a groove comprising a longitudinal opening spanning an exterior surface of the guide body;
wherein the groove is configured to guide translation of a surgical needle longitudinally along the guide body to a treatment location in a body lumen of a patient;
a slot spanning adjacent and exterior to the groove along the exterior surface of the guide body,
wherein the slot is configured to house the retainer so as to enclose said longitudinal opening when the retainer is disposed within the slot; and
wherein the retainer slideably mates with the slot such that the retainer may be removed from the guide body to expose the groove, thereby allowing the surgical needle to be separated from the guide body and imaging probe while the needle remains located at the treatment location.

17. The apparatus as recited in claim 16, wherein the guide body comprises an inner surface that conforms to the shape of the imaging probe.

18. The apparatus as recited in claim 16, wherein the guide body comprises a fastening mechanism to secure the apparatus to the imaging probe.

19. The apparatus as recited in claim 16, wherein the imaging probe comprises an ultrasound transducer.

20. The apparatus as recited in claim 19, wherein the slot terminates at a stop at the distal end of the guide body such that the retainer is restrained from forward motion past the stop and the distal end.

21. The apparatus as recited in claim 19:
wherein the groove emanates at a proximal opening of the proximal end and continues through the guide body to terminate at a distal opening at the distal end; and
wherein the guide body comprises a depression adjacent to the proximal opening of the groove to allow manipulation of the needle.

22. The apparatus as recited in claim 16, wherein the groove opens longitudinally out into the outer surface via the slot such that, when the retainer is not installed within the guide body, the needle may be laterally repositioned from the groove to a location outside the guide body.

23. The apparatus as recited in claim 16:
wherein the guide body has a proximal end and a distal end; and
wherein the retainer is installed in the guide body by positioning the retainer in an axial slot opening at the proximal end of the guide body, and sliding the retainer in the slot longitudinally along the guide body toward the distal end of the guide body.

* * * * *